US006620927B2

(12) United States Patent
Bulpitt et al.

(10) Patent No.: US 6,620,927 B2
(45) Date of Patent: Sep. 16, 2003

(54) THIOL-MODIFIED HYALURONAN

(75) Inventors: Paul C. A. Bulpitt, Stoneham, MA (US); Charles H. Sherwood, Sudbury, MA (US); Khalid K. Sadozai, Shrewsbury, MA (US)

(73) Assignee: Anika Therapeutics, Inc., Woburn, MA (US)

( * ) Notice: Subject to any disclaimer, the term of this patent is extended or adjusted under 35 U.S.C. 154(b) by 0 days.

(21) Appl. No.: 10/081,019

(22) Filed: Feb. 21, 2002

(65) Prior Publication Data

US 2002/0128512 A1 Sep. 12, 2002

Related U.S. Application Data

(60) Provisional application No. 60/271,023, filed on Feb. 22, 2001.

(51) Int. Cl.$^7$ .................................................. C07H 7/02
(52) U.S. Cl. .................. 536/123.1; 536/17.2; 536/18.7; 536/55; 536/55.1; 536/55.3; 536/106; 514/54
(58) Field of Search ............................... 536/17.2, 18.7, 536/55, 55.1, 55.3, 123.1, 106; 514/54

(56) References Cited

U.S. PATENT DOCUMENTS

| 2,832,756 A | | 4/1958 | Melamed |
| 5,099,013 A | * | 3/1992 | Balazs et al. ............... 536/55.1 |
| 5,118,813 A | * | 6/1992 | Reiner ......................... 548/336 |
| 5,356,883 A | | 10/1994 | Kuo et al. ..................... 514/54 |
| 5,616,568 A | * | 4/1997 | Pouyani et al. ................ 514/54 |
| 6,096,728 A | | 8/2000 | Collins et al. ................. 514/62 |
| 6,174,999 B1 | | 1/2001 | Miller et al. ................... 536/21 |

FOREIGN PATENT DOCUMENTS

| JP | 57009759 | 1/1982 |
| WO | WO 88/05436 | 7/1988 |
| WO | WO 94/02517 | 2/1994 |
| WO | WO 00/12146 | 3/2000 |
| WO | WO 02/09792 A1 | 2/2002 |

OTHER PUBLICATIONS

Kjær, A. and B. Christensen, isoThyocyanates XXVI. Straight–Chain ω–Methylathioalkyl isoThyocyanates and some Derivatives, *Acta Chem. Scand.* 11(8): 1298–1307 (1957).
Hermanson, G. T., *Bioconjugate Techniques* (Academic Press), pp. 104–107 (1996).
Schwartz, W. E., et al., "N–(β–iodethyl)trifluoroacetamide: A new reagentfor the aminoethylation of thiol groups in proteins," *Anal. Biochem.*, 106:43–48 (1980).
Bernkop–Schnürch, A., et al., "Development of controlled drug release systems based on thiolated polymers," *Journal of Controlled Release*, 66:39–44 (2000).
de Weers, O., et al., "Application of cystamine and N,N–Bis–(glycyl)cystamine as Linkers in Polysaccharide–Protein Conjugation," *Bioconjugate Chem.*, 9:309–315 (1998).
Williams, A., and Ibrahim, I.T., "Carboniimide Chemistry: Recent Advances," *Chem. Rev.*, 81(4):589–636 (1981).
March, J., "Eliminations: Reactions," *Advanced Organic Chemistry, Chapter 17: Reaction, Mechanisms, and Structure*, (NY: John Wiley & Sons), p. 1043 (1992).

* cited by examiner

*Primary Examiner*—Samuel Barts
*Assistant Examiner*—Ganapathy Krishnan
(74) *Attorney, Agent, or Firm*—Hamilton, Brook, Smith & Reynolds, P.C.

(57) ABSTRACT

The present invention relates to biscarbodiimides, thiourea derivatives, urea derivatives, and cross-linked hyaluronan derivatives having at least one intramolecular disulfide bond, and methods of preparation thereof. The invention also includes thiolated hyaluronan derivatives and salts thereof having at least one pendant thiol group or a modified pendant thiol group, and methods of preparation thereof. An example of a modified pendant thiol group is a sulfhydryl group linked to a small molecule such as a bioactive agent, for example a drug or pharmaceutically active moiety. A hyaluronan derivative having a sulfhydryl group linked to a pharmaceutically active moiety is useful as a sustained or controlled release drug delivery vehicle. Compositions containing the hyaluronan derivatives of the invention can reversibly viscosify in vivo or in vitro, in response to mild changes in condition, and are thus useful in ophthalmic surgery and in tissue engineering.

6 Claims, 8 Drawing Sheets

THIOL-MODIFIED HYALURONAN

RELATED APPLICATION

This application claims the benefit of U.S. Provisional Application No. 60/271,023, filed on Feb. 22, 2001, the entire teachings of which are incorporated herein by reference in their entirety.

BACKGROUND OF THE INVENTION

Hyaluronic acid, also referred to as "HA," is a naturally occurring, water soluble polysaccharide comprising disaccharide units of D-glucuronic acid (GlcUA) and N-acetyl-D-glucosamine (GlcNAc), which are alternately linked, forming a linear polymer. High molecular weight HA may comprise 100 to 10,000 disaccharide units. HA often occurs naturally as the sodium salt, sodium hyaluronate. HA, sodium hyaluronate, and preparations of either HA or sodium hyaluronate are often referred to as "hyaluronan." As used herein, the terms "HA" and "hyaluronan" also refer to any of the other hyaluronate salts, including, but not limited to, potassium hyaluronate, magnesium hyaluronate, and calcium hyaluronate.

HA is a major component of the extra-cellular matrix and is widely distributed in animal tissues. Naturally occurring HA generally has a molecular weight range of about between $6 \times 10^4$ to about $1.2 \times 10^7$ daltons. It has excellent biocompatibility and does not give a foreign body reaction when implanted or injected into a living body. An aqueous solution of hyaluronan is viscous even at relatively low solute concentrations.

Methods of preparing commercially available hyaluronan are well known. Also known are various methods of coupling HA and cross-linking HA to reduce the water solubility and diffusibility of HA, and to increase the viscosity of HA. See, for example, U.S. Pat. Nos. 5,356,883 and 6,013,679, the teachings of which are incorporated herein by reference in their entireties.

Chemically modified HA has been used as a surgical aid to prevent post-operative adhesions of tissues.

Currently there is interest in developing chemically modified HA for delivery of bioactive agents including, for example, therapeutic agents or drugs and biological probes. A major challenge is the development of a delivery vehicle that will provide the appropriate level of bioavailability of a therapeutic agent at the affected area to achieve a desired clinical result. The bioavailability of a drug depends upon the nature of the drug, the drug delivery vehicle used, and the route of delivery, for example, oral, topical, transdermal, mucosal, administration by injection, administration by inhalation, or administration by a combination of two or more of these routes. The bioavailability may be low as a result of, for example, the degradation of the drug by stomach acid, elimination from the gastrointestinal tract, or high aqueous solubility of the drug. As a result, frequent administration may be required, and the amount of drug delivered with each administration may be high, leading to an increase in the occurrence of damaging side effects.

Highly viscous cross-linked HA derivatives are sometimes used as an aid in ophthalmic surgery, such as intraocular lens implantation, glaucoma surgery, vitrectomy, and repair of retinal detachment. However, because of its high viscosity and stability, this cross-linked HA does not readily clear out through the trabecular meshwork, the outlet for aqueous humor egress. Blockage of the trabecular meshwork by the cross-linked HA may contribute to post-operative increases in intraocular pressure, including intraocular spikes (IOPs), the increases in pressure sometimes causing damage to the optic nerve, as well as damage to the cornea.

Cross-linked HA that is highly viscous is also used as a scaffold for tissue engineering in vitro or guided tissue regeneration or augmentation in vivo. Because of the high viscosity and stability of this HA derivative, however, recovery of cells grown on the cross-linked HA can be problematic.

SUMMARY OF THE INVENTION

The present invention relates to compositions including, for example, a biscarbodiimide having an intramolecular disulfide bond. The invention inter alia also includes the following embodiments, alone or in combination. In one embodiment, a biscarbodiimide having an intramolecular disulfide bond is formed by a method including reacting an isothiocyanate with cystamine (2,2'-dithiobis(ethylamine), $(H_2NCH_2CH_2)_2S_2$), thereby forming a thiourea derivative, which is then reacted with an oxidizing agent or a dehydrosulfuration agent, thereby forming a biscarbodiimide having an intramolecular disulfide bond.

In another embodiment, a biscarbodiimide having an intramolecular disulfide bond is formed by a method including reacting an isocyanate with cystamine, thereby forming a urea derivative, which is then reacted with a dehydrating agent, thereby forming a biscarbodiimide having an intramolecular disulfide bond.

In a particular embodiment, the biscarbodiimide having an intramolecular disulfide bond is represented by Structural Formula (1):

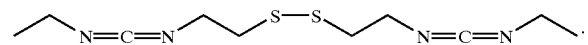

In another embodiment, a biscarbodiimide having an intramolecular disulfide bond is formed by a method including reacting an isothiocyanate with 2-aminophenyl disulfide or 4-aminophenyl disulfide, thereby forming a thiourea derivative, which is then reacted with an oxidizing agent or a dehydrosulfuration agent, thereby forming a 1,1'dithiophenylene bis(ethylcarbodiimide).

In a particular embodiment, a biscarbodiimide having an intramolecular disulfide bond is represented by Structural Formula (2) or (3):

Formula (2)

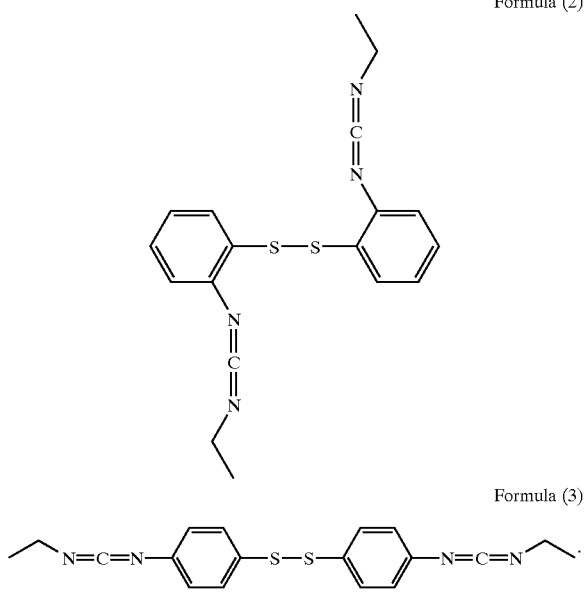

Formula (3)

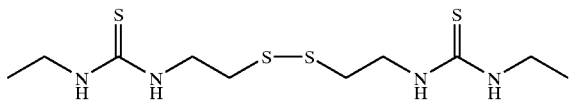

Another embodiment is a thiourea derivative having an intramolecular disulfide bond, the thiourea derivative formed by reacting an isothiocyanate with cystamine. In a particular embodiment, a thiourea derivative having an intramolecular disulfide bond is represented by Structural Formula (4):

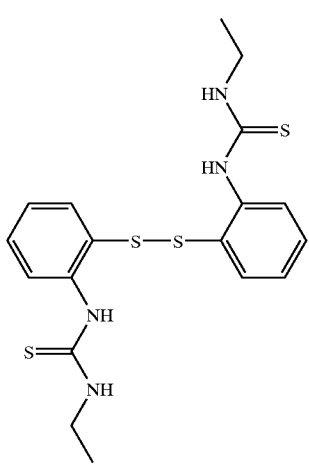

Yet another embodiment is a thiourea derivative having an intramolecular disulfide bond, the thiourea derivative formed by reacting an isothiocyanate with 2-aminophenyl disulfide or 4-aminophenyl disulfide, thereby forming the thiourea derivative.

In a particular embodiment, a thiourea derivative having an intramolecular disulfide bond is represented by Structural Formula (5) or (6):

Formula (5)

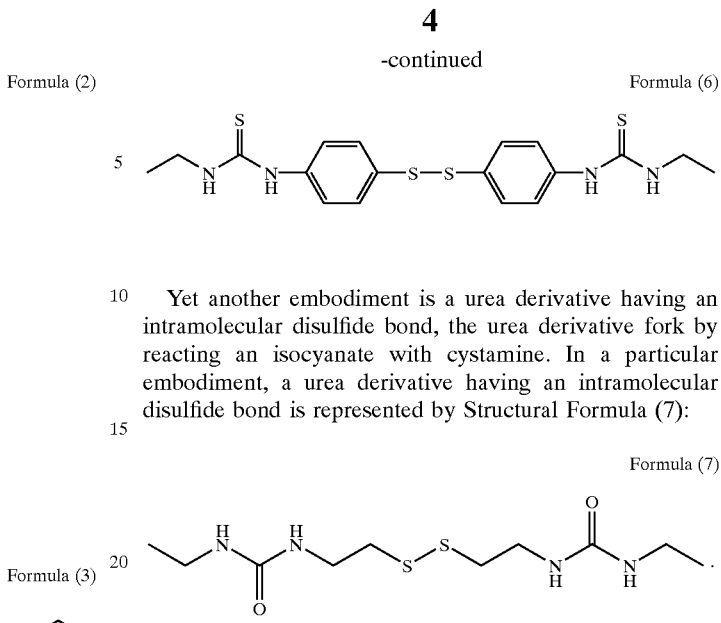

Formula (6)

Yet another embodiment is a urea derivative having an intramolecular disulfide bond, the urea derivative fork by reacting an isocyanate with cystamine. In a particular embodiment, a urea derivative having an intramolecular disulfide bond is represented by Structural Formula (7):

Formula (7)

Another embodiment includes a cross-linked hyaluronan derivative containing at least one intramolecular disulfide bond, wherein the derivative is the product of a reaction between the precursor of the derivative and a biscarbodiimide having an intramolecular disulfide bond. In a particular embodiment, a cross-linked hyaluronan derivative containing at least one intramolecular disulfide bond is the product of a reaction between hyaluronic acid or a salt thereof and a biscarbodiimide having an intramolecular disulfide bond. In another embodiment, a cross-linked hyaluronan derivative containing at least one intramolecular disulfide bond is the product of a reaction between hyaluronic acid or a salt thereof and a biscarbodiimide represented by Structural Formula (1):

A particular embodiment includes a cross-linked hyaluronan derivative represented by Structural Formula (8) and salts thereof:

Formula (8)

In another embodiment, a thiolated hyaluronan derivative and salts thereof have at least one pendant thiol group, the thiolated hyaluronan derivative formed as a product of a reaction between a cross-linked hyaluronan containing at least one intramolecular disulfide bond and a reducing agent. In a particular embodiment, a thiolated hyaluronan derivative having at least one pendant thiol group may be represented by Structural Formula (9):

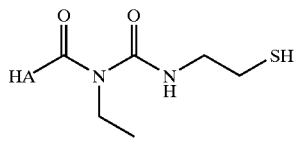

Another embodiment is a compound that may be represented by Structural Formula (10) and salts thereof:

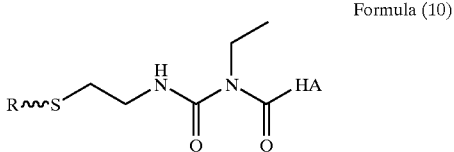

Formula (10)

wherein R is a small molecule or monovalent moiety selected from alkyl, aryl, alkylene, halo, alkyl halide, amine, ethylamine, alkoxy, aryloxy, alkaryloxy, carboxylate, borate, and phenylborate.

Another embodiment is a compound that may be represented by Structural Formula (10) and salts thereof:

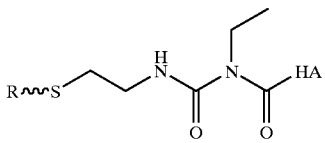

wherein R is a drug or pharmaceutically active moiety.

Another embodiment of the invention is a method of preparing a biscarbodiimide compound represented by Structural Formula (1), including the steps of reacting ethyl isothiocyanate with cystamine, thereby forming a thiourea intermediate, 2,2'dithiobis (N-ethyl(N'-ethylthiourea)), having Structural Formula (4); and reacting the thiourea intermediate with an oxidizing agent or a dehydrosulfuration agent, thereby forming a biscarbodiimide compound represented by Structural Formula (1).

Another embodiment is a method of preparing a biscarbodiimide compound represented by Structural Formula (1), including the steps of reacting ethyl isocyanate with cystamine, thereby forming a urea intermediate, 2,2'dithiobis (N-ethyl(N'-ethylurea)), having Structural Formula (7); and reacting the urea intermediate with a dehydrating agent, thereby forming a compound represented by Structural Formula (1).

Another embodiment is a method of preparing a biscarbodiimide compound represented by Structural Formula (2) or (3), including the steps of reacting ethyl isothiocyanate with 2-aminophenyl disulfide or 4-aminophenyl disulfide, thereby forming a thiourea intermediate having Structural Formula (5) or (6); and reacting the thiourea intermediate with an oxidizing agent or a dehydrosulfuration agent, thereby forming 1,1'dithio-o-phenylene bis (ethylcarbodiimide), having Structural Formula (2), or 1,1'dithio-p-phenylene bis(ethylcarbodiimide), having Structural Formula (3).

Another embodiment is a method of preparing a thiolated hyaluronan derivative having Structural Formula (9), comprising the steps of reacting a biscarbodiimide compound represented by Structural Formula (1), with hyaluronic acid or a salt thereof, to form a cross-linked hyaluronic acid derivative of Structural Formula (8); and reacting the derivative of Structural Formula (8) with tris(2-carboxyethyl) phosphine hydrochloride, thereby forming the thiolated hyaluronan derivative having Structural Formula (9).

Yet another embodiment is a method of cross-linking pendant thiol groups on a thiolated hyaluronic acid derivative to form a hydrogel, the method including the step of: reacting a thiolated hyaluronan derivative of structural formula (9),

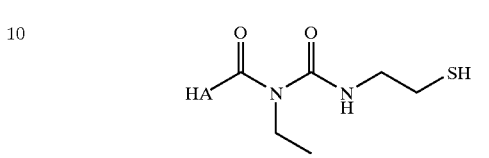

with a homobifunctional cross-linker.

The present invention has many advantages. For example, the hyaluronan derivative represented by structural formula (10) and salts thereof, wherein R is a drug or pharmaceutically active moiety is an embodiment which can function as a drug delivery vehicle. The hyaluronan derivative of this embodiment can bind to bioactive agent R without significantly reducing its activity, and is also capable of slowly releasing the bioactive agent at a target tissue site. With such a slow-release delivery vehicle, bioavailability can be more controlled and the dosing kept more even than with many currently available delivery systems. Further, use of a slow-release delivery vehicle allows the amount of drug administered at one time to be kept low to minimize side effects, and the frequency of administration to be reduced.

A hyaluronan derivative according to the invention also provides several advantages when used in ophthalmic surgery and in tissue engineering or tissue regeneration. The hyaluronan derivative according to one embodiment of the invention is a cross-linked, biocompatible, biodegradable material having a sufficiently high viscosity, resilience, other good mechanical properties, and sufficient stability to perform its intended function, but can be decreased in viscosity and decreased in stability. When used in ophthalmic surgery, the derivative can be decreased in viscosity so that it can clear out through the trabecular meshwork and be absorbed by the body. When used as a scaffold to grow tissue, the viscosity of the derivative can be decreased, and as the derivative disintegrates, it can become disassociated from cells grown thereon.

BRIEF DESCRIPTION OF THE DRAWINGS

The foregoing and other features and advantages of the invention will be apparent from the following more particular description of preferred embodiments of the invention, as illustrated in the accompanying drawings.

DETAILED DESCRIPTION OF THE INVENTION

Figure 1:
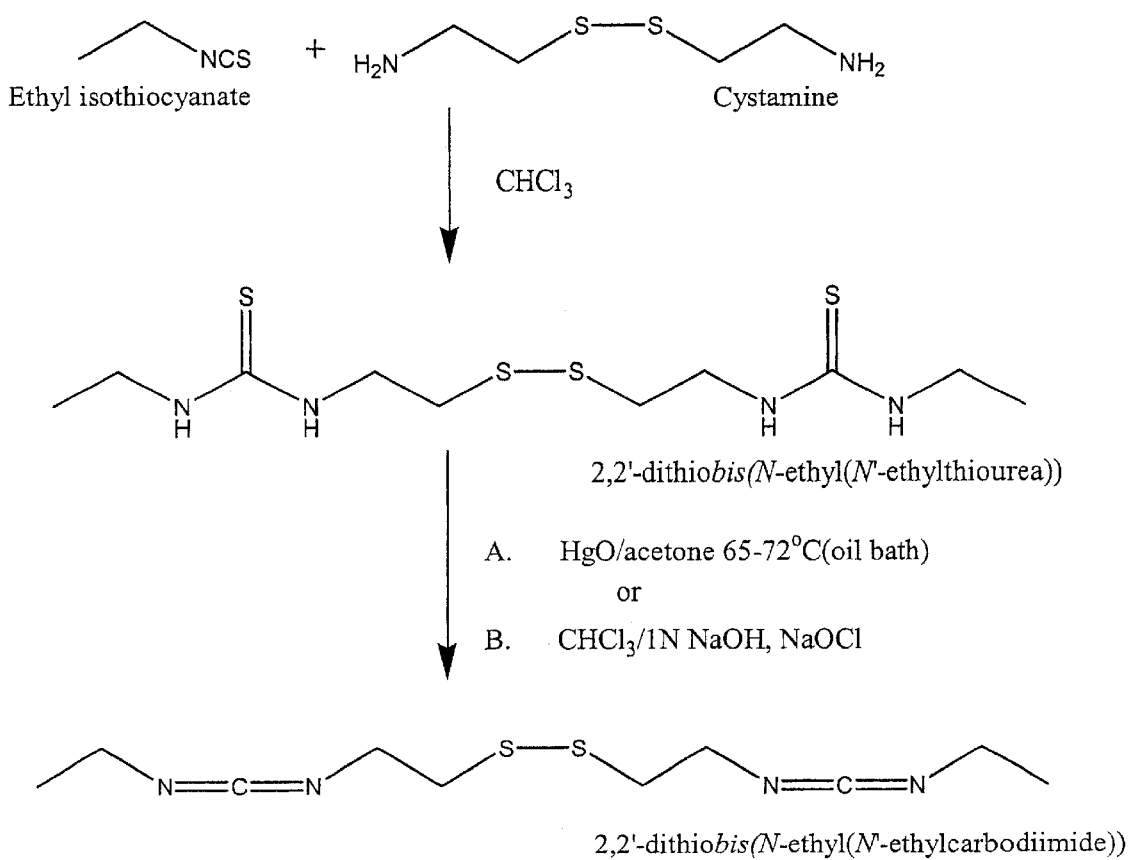
FIG. 1 is a representation of a general reaction scheme for the synthesis of 2,2'-dithiobis(N-ethyl (N' ethylcarbodiimide)) by one embodiment of the method of the invention, Route 1, using ethyl isothiocyanate.

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The present invention is directed to compositions and methods of preparation thereof, the compositions having an intramolecular disulfide bond, a pendant thiol group, or a modified pendant thiol group.

Embodiments of the invention include, for example, biscarbodiimides having an intramolecular disulfide bond or a masked thiol group. As used herein, the terms "masked thiol," "masked thiol group," and grammatical variations thereof, refer to an intramolecular disulfide bond which may be converted to a thiol group by processes such as, for example, oxidation, dehydrosulfuration, dehydration, and other methods known in the art. Other embodiments include, for example, thiourea derivatives, urea derivatives, and cross-linked hyaluronan derivatives, all having at least one intramolecular disulfide bond or masked thiol group, as well as methods of synthesizing such compounds. As used herein, the terms "cross-linked hyaluronan derivative," "cross-linked hyaluronic acid derivative," "cross-linked hyaluronan," and "cross-linked hyaluronic acid" have the same meaning, an include an N-acylurea. The invention also provides methods for either reversible or irreversible cross-linking of hyaluronan, so that the resulting hyaluronan gel viscosity and other properties can be readily manipulated.

Embodiments of the invention include novel thiolated hyaluronan derivatives and salts thereof, having at least one pendant thiol group, also referred to as a sulfhydryl group. As used herein, the terms "thiolated hyaluronan derivative," "thiolated hyaluronic acid derivative," "thiolated hyaluronan," and "thiolated hyaluronic acid" have the same meaning and include an N-acylurea. Yet other embodiments include for example, novel thiolated hyaluronan derivatives and salts thereof, having at least one sulfhydryl group linked to a small molecule, such as a bioactive agent, and include an N-acylurea. The invention also provides methods for functionalizing hyaluronan through reaction with a thiol group on thiolated hyaluronan. A small molecule such as, for example, a bioactive agent, can be attached to a functionalized hyaluronan molecule by substituting the bioactive agent for a hydrogen of at least one thiol group. Methods for substituting a bioactive agent for a hydrogen of a thiol group on a polymer are well known to those of ordinary skill in the art. See, for example, "Development of controlled drug release systems based on thiolated polymers," Bernkop-Schnürch, A. et al., *Journal of Controlled Release,* 2000, 66, 39–48, the entire teachings of which are incorporated herein by reference in their entirety. Thiolated hyaluronan according to an embodiment of the invention, has mucoadhesive properties. Such mucoadhesive properties can enhance both the controlled release of a bioactive agent that has replaced a hydrogen on at least one of the thiol groups, as well as the localization of the delivery of the bioactive agent to the desired site.

In general, a novel biscarbodiimide having an intramolecular disulfide bond, such as, for example, 2,2'-dithiobis (N-ethyl (N'ethylcarbodiimide)), a biscarbodiimide having Structural Formula (1):

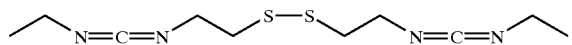

may be synthesized according to an embodiment of the invention by at least one of two routes Route 1, Synthesis of a Thiourea Derivative Intermediate and a Biscarbodiimide of the Invention The first route, which is represented schematically in FIG. 1, is explained in greater detail below and in Example 1. Typically, the synthesis is carried out by reacting an isothiocyanate, for example, ethyl isothiocyanate (NCS), propyl isothiocyanate, butyl isothiocyanate, tert-butyl isothiocyanate, or phenyl isothiocyanate with cystamine, to form a novel thiourea derivative having an intramolecular disulfide bond. In a particular embodiment, if ethyl isothiocyanate is reacted with cystamine, the novel product formed is 2,2'-dithiobis(N-ethyl(N'-ethylthiourea)), having a structural formula represented by Formula (4), and having an intramolecular disulfide bond:

Formula (4)

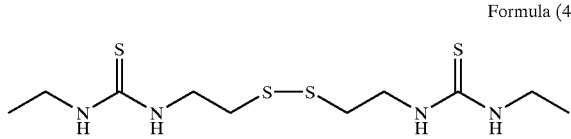

According to an embodiment, the novel thiourea derivative intermediate is then reacted with an oxidizing agent or a dehydrosulfuration agent, thereby forming another novel compound, a biscarbodiimide having an intramolecular disulfide bond. An example of a suitable oxidizing agent is a hypochlorite, such as sodium hypochlorite. Other suitable oxidizing agents include, for example, N-bromosuccinimide, 1-chlorobenzothiazole, and N-chloroamidines.

An example of a suitable dehydrosulfuration agent is mercury II oxide. Other suitable dehydrosulfuration agents are well known in the art and include phosgene, diethyl azodicarboxylate-triphenylphosphine, lead oxide, silver oxide, activated aluminum oxide, and quinones. Yet other dehydrosulfuration agents include, but are not limited to, thionyl chloride, sulfenyl chloride, chlorosulfonic acid, $SCl_2$, $S_2Cl_2$, and phosphorus halides.

The above reaction steps, according to an embodiment of the invention, for forming both a novel thiourea derivative intermediate having an intramolecular disulfide bond, and 2,2'-dithiobis(N-ethyl (N'ethylcarbodiimide)), a novel biscarbodiimide having an intramolecular disulfide bond, by way of Route 1 may be summarized according to the reaction scheme shown in FIG. 1.

Embodiments include other disulfide-containing biscarbodiimides of the general formula: $R^1-N=C=N-R^2-S-S-R^2-N=C=N-R^1$, wherein $R^1$ and $R^2$ may be the same or different and may include hydrocarbyl, aryl, substituted-hydrocarbyl, substituted aryl, and the like.

The term "hydrocarbyl" as used herein means the monovalent moiety obtained upon removal of a hydrogen atom from a parent hydrocarbon. Representatives of hydrocarbyls include, for example, alkyls of 1 to 25 carbon atoms, inclusive, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonodecyl, eicosyl, heneicosyl, docosyl, tricosyl, tetracosyl, pentacosyl and the isomeric forms thereof. Other representatives of hydrocarbyls include aryls. The term "aryl" as used herein refers to the monovalent moiety obtained upon removal of a hydrogen atom from a parent aromatic compound. Representatives of aryl groups may have, for example, 6 to 25 carbon atoms, inclusive, such as phenyl, tolyl, xylyl, naphthyl, biphenylyl, triphenylyl, and the like. Yet other representatives of hydrocarbyls include cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, and isomeric forms thereof. Preferably, hydrocarbyl has 6 to 14 carbon atoms, inclusive.

The term "substituted hydrocarbyl" as used herein means the hydrocarbyl moiety as previously defined wherein one or more hydrogen atoms have been replaced with a chemical group which does not adversely affect the desired preparation of the product derivative. Representative of such groups are amino and alkyl.

Representatives of substituted aryls according to an embodiment include, for example, arylalkyl of 7 to 25 carbon atoms, inclusive, such as benzyl ($C_6H_5CH_2$), phenylethyl, phenylpropyl, phenylbutyl, phenylhexyl, naphthylalkyl and the like.

Methods of preparing biscarbodiimides are described in U.S. Pat. Nos. 6,013,679; 2,946,819; 3,231,610; 3,502,722; 3,644,456; 3,972,933; 4,014,935; 4,066,629; 4,085,140; 4,096,334; and 4,137,386, the teachings of which are incorporated herein by reference in their entireties.

In order to prepare biscarbodiimides according to an embodiment of the general formula: formula: $R^1-N=C=N-R^2-S-S-R^2-N=C=N-R^1$, wherein $R^1$ and $R^2$ may be the same or different and may include, for example, hydrocarbyl, substituted aryl, substituted aryl, and the like, reaction Route 1 may be followed, starting with an aminophenyl disulfide, such as, for example, 2-aminophenyl disulfide or 4-aminophenyl disulfide and an isothiocyanate.

In a particular embodiment, a thiourea derivative having an intramolecular disulfide bond is formed by reacting an aminophenyl disulfide, such as, for example, 2-aminophenyl disulfide or 4-aminophenyl disulfide and an isothiocyanate, such as, for example, ethyl isothiocyanate, propyl isothiocyanate, butyl isothiocyanate, sec-butyl isothiocyanate, tert-butyl isothiocyanate, or phenyl isothiocyanate.

Figure 3:
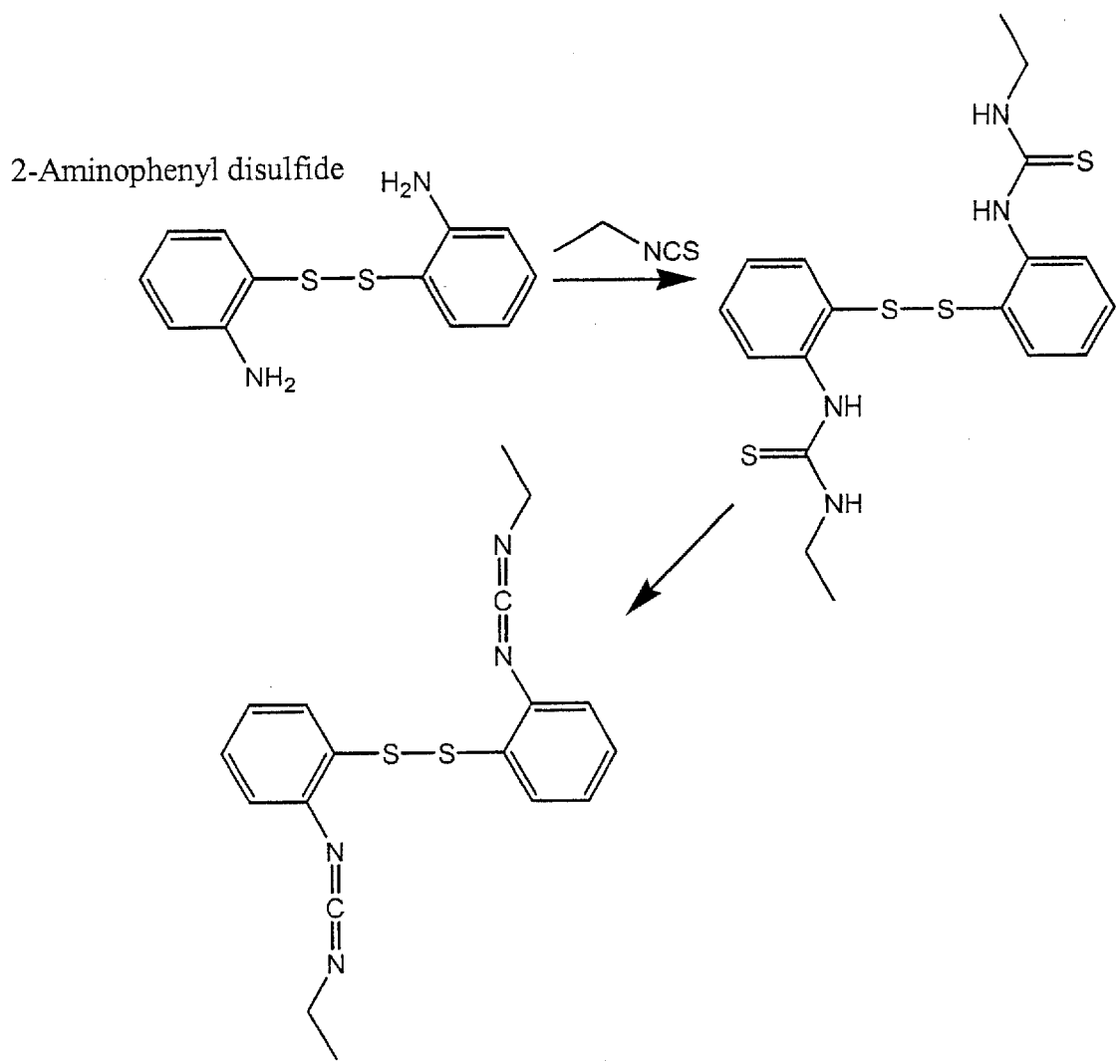
FIG. 3 is a representation of a general reaction scheme for the synthesis of 1,1'dithio-o-phenylene bis (ethylcarbodiimide) by Route 1.

For example, as shown schematically in FIG. 3, an embodiment of a general reaction scheme for the synthesis of 1,1'dithio-o-phenylene bis(ethylcarbodiimide), a compound represented by Structural Formula (2), includes the steps of reacting ethyl isothiocyanate with 2-aminophenyl disulfide, thereby forming a thiourea derivative intermediate having Structural Formula (5); and reacting the thiourea intermediate with an oxidizing agent or a dehydrosulfuration agent, thereby forming 1,1'dithio-o-phenylene bis (ethylcarbodiimide), having Structural Formula (2).

Figure 4:
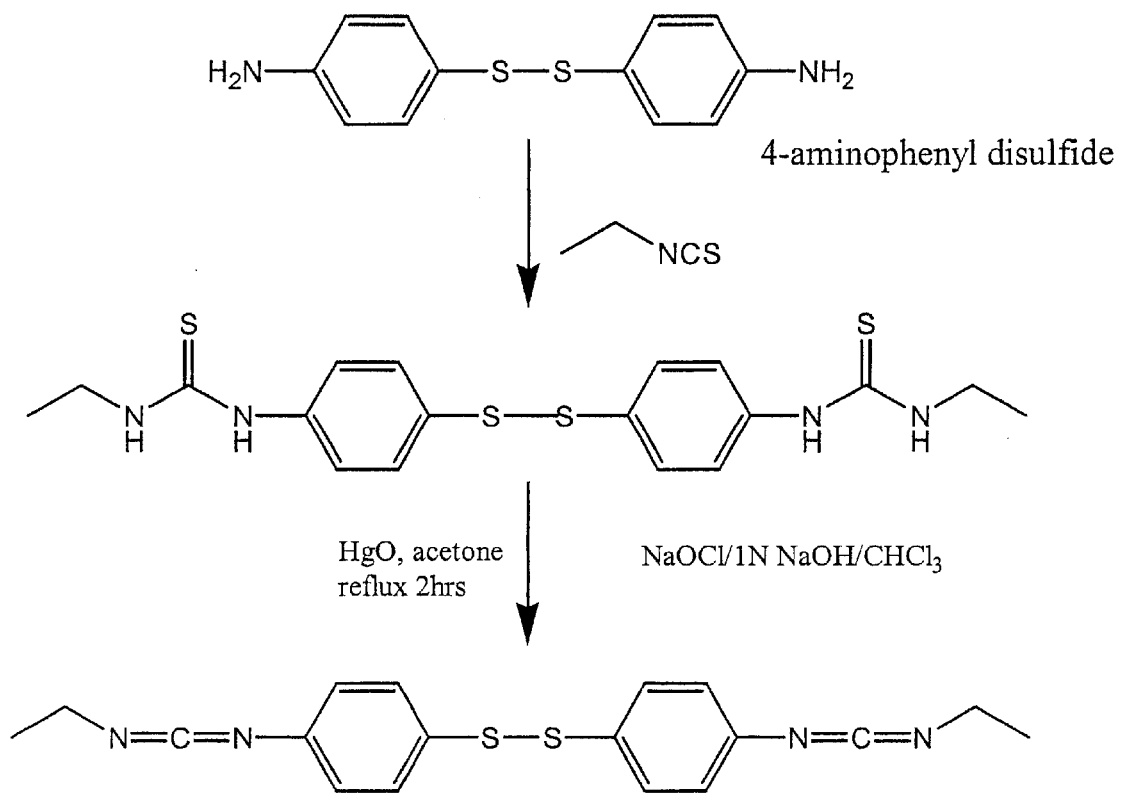
FIG. 4 is a representation of a general reaction scheme for the synthesis of 1,1'dithio-p-phenylene bis (ethylcarbodiimide) by Route 1.

Another example of the preparation of a biscarbodiimide having an intramolecular disulfide bond and an $R^2$ which is a substituted aryl, according to an embodiment, using reaction Route 1 is shown schematically in FIG. 4. FIG. 4 represents a general reaction scheme for the synthesis of 1,1'dithio-p-phenylene bis(ethylcarbodiimide), a compound represented by Structural Formula (3). The scheme includes the steps of reacting ethyl isothiocyanate with 4-aminophenyl disulfide, thereby forming a thiourea intermediate having Structural Formula (6); and reacting the thiourea intermediate with an oxidizing agent or a dehydrosulfuration agent, thereby forming 1,1'dithio-p-phenylene bis(ethylcarbodiimide), having Structural Formula (3).

Those skilled in the art will know, or will be able to ascertain with no more than routine experimentation, which oxidizing agents or dehydrosulfuration agents are suitable for use in Route 1 syntheses. For example, the thiourea intermediate formed according to an embodiment by reacting ethyl isothiocyanate, propyl isothiocyanate, butyl isothiocyanate, tert-butyl isothiocyanate, or phenyl isothiocyanate with an aminophenyl disulfide may be further converted to a biscarbodiimide having an intramolecular disulfide bond by oxidation with a hypochlorite such as NaOCl in 1N NaOH. Other examples of suitable oxidizing agents include, but are not limited to, N-bromosuccinimide, 1-chlorobenzothiazole, and N-chloroamidines. Examples of dehydrosulfuration agents that are suitable for use in Route 1 syntheses include, but are not limited to, mercury II oxide, phosgene, diethyl azodicarboxylate-triphenylphosphine, lead oxide, silver oxide, activated aluminum oxide, quinones, thionyl chloride, sulfenyl chloride, chlorosulfonic acid, $SCl_2$, $S_2Cl_2$, and phosphorus halides.

In other embodiments, novel thiourea intermediates having at least one phenyl group and at least one intramolecular disulfide bond, as well as novel biscarbodiimides having at least one phenyl group and at least one intramolecular disulfide bond, can be formed by reacting propyl isothiocyanate, butyl isothiocyanate, tert-butyl isothiocyanate, or phenyl isothiocyanate with an aminophenyl disulfide, thereby forming a thiourea intermediate; and reacting the thiourea intermediate with an oxidizing agent or a dehydrosulfuration agent, thereby forming a biscarbodiimide having both an intramolecular disulfide bond and an $R^2$ which is a substituted aryl. Examples of suitable oxidizing agents and dehydrosulfuration agents are provided above; other examples are known by those skilled in the art, or may be readily ascertained with no more than routine experimentation.

In yet other embodiments, thiourea intermediates and biscarbodiimides having at least one intramolecular disulfide bond can be formed according to the general scheme of reaction Route 1 by reacting an isothiocyanate with other disulfides, such as, for example, a disulfide having the general formula, $H_2N-R-S-S-R'-NH_2$, wherein R and R' are the same or different and are hydrocarbyl such as, for example, alkyl, substituted alkyl, phenyl, and substituted phenyl. The terminal amines of the disulfide according to an embodiment must be primary amines. Having provided the above guidelines as well as the below exemplification, those skilled in the art will know, or will be able to ascertain with no more than routine experimentation, other disulfides which are suitable for use in Route 1 syntheses.

Figure 2:
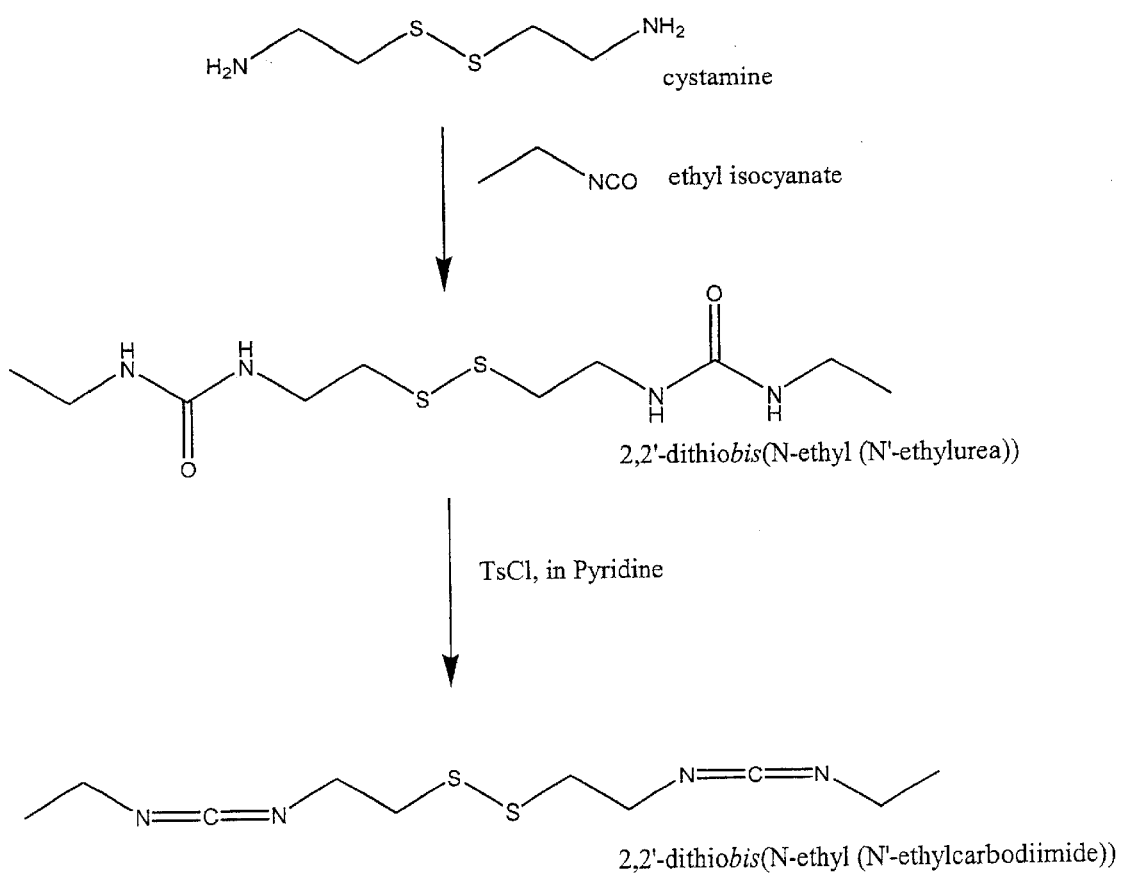
FIG. 2 is a representation of a general reaction scheme for the synthesis of 2,2'-dithiobis(N-ethyl (N' ethylcarbodiimide)) by another embodiment of the method of the invention, Route 2, using ethyl isocyanate.

Route 2: Synthesis of a Urea Intermediate and a Biscarbodiimide of the Invention The second route, which is represented schematically in FIG. 2, is explained in greater detail below and in Example 3(a) and (b). Typically the synthesis carried out by reacting an isocyanate, for example, ethyl isocyanate (NCO), propyl isocyanate, butyl isocyanate, sec-butyl isocyanate, tert-butyl isocyanate, or phenyl isocyanate, with cystamine, to form a novel urea intermediate, a urea derivative having an intramolecular disulfide bond. In a particular embodiment, described in detail in Example 3, if ethyl isocyanate is reacted with cystamine, the novel intermediate product formed is 2,2'-dithiobis(N-ethyl(N'-ethylurea)), having a structural formula represented by Formula (7), and having an intramolecular disulfide bond:

Formula (7)

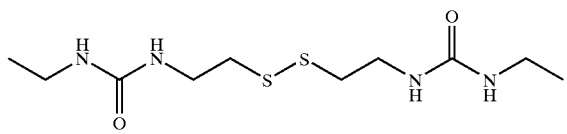

According to an embodiment, further described in Example 3 (b), the urea derivative is then reacted with a dehydrating agent, such as p-toluenesulfonyl chloride (TsCl) in pyridine, thereby forming a biscarbodiimide having an intramolecular disulfide bond. Other suitable dehydrating agents include, among others, $POCl_3$, $PCl_5$, $P_2O_5$ in pyridine, p-toluenesulfonyl chloride in a phase-transfer catalysis system, and $Ph_3PBr_2$-$Et_3N$. Those skilled in the art will know, or will be able to ascertain with no more than routine experimentation, yet other dehydrating agents suitable for use in Route 2 syntheses.

The reaction steps for forming 2,2'-dithiobis(N-ethyl (N'ethylcarbodiimide) by way of Route 2 may be represented generally according to the reaction scheme shown in FIG. 2.

In an alternative embodiment, in lieu of cystamine, another disulfide such as, for example, an aminophenyl disulfide can be reacted with an isocyanate according to the Route 2 scheme to form a urea intermediate, that is then reacted with a dehydrating agent, such as p-toluenesulfonyl chloride (TsCl) in pyridine, thereby forming a novel biscarbodiimide having an intramolecular disulfide bond.

Other Disulfides for Use in Route 2 Synthesis

In yet other embodiments, a disulfide having the general formula, $H_2N$—R—S—S—R'—$NH_2$, wherein R and R' are the same or different and are hydrocarbyl such as, for example, alkyl, substituted alkyl, phenyl, and substituted phenyl, can be used to react with an isocyanate for Route 2 synthesis of a novel biscarbodiimide.

Preparation of Cross-linked Hyaluronan Derivatives of the Invention Containing at Least One Intramolecular Disulfide Bond According to an embodiment of the invention, a cross-linked hyaluronan derivative containing at least one intramolecular disulfide bond can be produced by a reaction between the precursor of the cross-linked hyaluronan derivative and a biscarbodiimide having an intramolecular disulfide bond. A "precursor of a cross-linked hyaluronan derivative," as the expression and grammatical variations thereof are used herein, in one embodiment, means a polysaccharide that can be cross-linked with a biscarbodiimide having an intramolecular disulfide bond. An example of a precursor of a cross-linked hyaluronan derivative is hyaluronic acid. Another example of a precursor of the cross-linked hyaluronan derivative is a salt of hyaluronic acid. A "cross-linked hyaluronan derivative," and "derivatized hyaluronic acid," as the terms are used herein, mean hyaluronic acid or a salt thereof that has been derivatized with a biscarbodiimide having an intramolecular disulfide bond, the derivatized hyaluronic acid including an N-acylurea. A biscarbodiimide is a cross-linking agent. A "cross-linking agent," as that phrase is used herein, is a molecule containing two or more functional groups that can react with different chains of a polymer, such as, for example, hyaluronic acid or a salt thereof. Preferably, the hyaluronic acid derivative having an intramolecular disulfide bond is prepared by reacting hyaluronic acid, or a salt thereof, with a biscarbodiimide having an intramolecular disulfide bond, in the absence of a nucleophile or a polyanionic polysaccharide other than hyaluronic acid. A "nucleophile," as that term is used herein, is any molecule possessing an electron rich functional group (such as a primary amine). A "polyanionic polysaccharide," as that term is used herein, is a polysaccharide containing more than one negatively charged group, e.g., a carboxyl group.

The hyaluronic acid derivative having an intramolecular disulfide bond includes an N-acylurea. The reaction of hyaluronic acid or a salt thereof with a biscarbodiimide having an intramolecular disulfide bond, in the presence of an available proton, is believed to comprise protonation in the first step. The acid anion then attaches to the carbon atom of the cation formed, resulting in the formation of an O-acylisourea intermediate. The acyl group in the intermediate migrates from the oxygen atom to a nitrogen atom to produce the N-acylurea derivative of the hyaluronic acid or salt. Generally the O-to-N migration is incomplete, resulting in a product reaction mixture of both the N-acylurea and the O-acylisourea. The mixed products may be used separately or together to prepare the compositions according to embodiments of the invention.

In one embodiment, the cross-linked hyaluronan derivative is biocompatible. A "biocompatible" substance, as that term is used herein, is one that has no medically unacceptable toxic or injurious effects on biological function. In another embodiment, the cross-linked hyaluronan derivative is both biocompatible and biodegradable. A "biodegradable" substance, as that term is used herein, is one that is capable of being decomposed by natural biological processes.

The hyaluronic acid or salts of hyaluronic acid used as starting compositions for the reaction according to an embodiment of the invention generally have an average molecular weight range of from between about $6 \times 10^4$ to about $1.2 \times 10^7$ daltons. Hyaluronic acid from any of a variety of sources, including hyaluronic acid extracted from animal tissues or harvested as a product of bacterial fermentation, can be used as a starting material. Alternatively, the hyaluronic acid used to make the composites of this invention can be produced in commercial quantities by bioprocess technology, as described, for example, in Nimrod et al., PCT Publication No. WO 86/04355, the entire teachings of which are incorporated herein by reference in their entirety.

The reaction can be carried out at a temperature range of between about 0° C. and about 60° C., preferably between about 15° C. and about 30° C.

Hyaluronic acid or its salt is dissolved in water to make an aqueous solution. Preferably, the concentration of hyaluronic acid in this first aqueous solution is in the range of between about 1 mg/ml solution to about 15 mg/ml solution. More preferably, the reactions are carried out with a range of between about 4 to about 8 mg of hyaluronic acid per milliliter. The optimal concentration of hyaluronic acid is about 4 to about 6 mg/ml. The precise concentration used will vary depending on the molecular weight of the hyaluronic acid. At significantly lower concentrations, the reactions are slower and less effective. At significantly higher hyaluronic acid concentrations, the end product may be difficult to handle due to the increase in viscosity. One skilled in the art will be able to determine, with no more than routine experimentation, an acceptable concentration of hyaluronic acid to be used for a particular embodiment. Examples of acceptable concentrations of hyaluronic acid are described in U.S. Pat. No. 5,356,883, to Kuo et al, the teachings of which are incorporated herein by reference in their entirety.

The hyaluronic acid can be dissolved in distilled water, or in 0.9% saline. Alternatively, it can be dissolved in a solvent comprising about 100–60% water and about 0–40% dimethylformamide (DMF).

The pH of the hyaluronic acid solution is then adjusted by the addition of a suitable acid, for example, hydrochloric acid, 0.1M, so that the aqueous hyaluronic acid solution preferably has a pH of between about 4.0 and about 8.0, more preferably between about 4 and about 6, and optimally between about 4.75 and about 5.80.

Once the pH of the aqueous hyaluronic acid solution has been adjusted, the biscarbodiimide having an intramolecular disulfide bond can be added. Generally an excess of the stoichometric proportion of biscarbodiimide is advantageous to promote the desired reaction. Preferably the molar equivalent ratio of the hyaluronic acid to the biscarbodiimide is equal to or greater than about 3.3.

Preferably, the biscarbodiimide is dissolved in an appropriate water-mixable solvent, such as, for example, acetone, and added drop-wise, over a period of, for example, about 2 to 3 hours. As the biscarbodiimide and the hyaluronic acid are mixed, the pH of the solution generally will increase. Gels with various desired physical properties can be obtained by simply allowing the pH to rise as the reaction proceeds. By dropwise addition of 0.1 M HCl, the pH is gradually reduced back to about 4.75. Sodium chloride is then added to the reaction mixture to about 5% NaCl. The reaction mixture is stirred for about a half hour. The reaction mixture is then poured onto ethanol (3 volume equivalents of ethanol to one volume of aqueous solution). A precipitate of cross-linked hyaluronic acid having an intramolecular disulfide bond forms, and can be collected by filtration and dried under reduced pressure.

Example 2 provides details of the cross-linking of high molecular weight hyaluronic acid with 2,2'-dithiobis(N-ethyl (N'ethylcarbodiimide)) according to one embodiment of the invention, to form a novel compound having an intramolecular disulfide bond, the compound represented by Structural Formula 8. On reaction with the hyaluronan, the biscarbodiimide rearranges to stable N-acyl urea-based cross-links containing a disulfide bridge. The addition of at least one disulfide bridge along the hyaluronan polymer backbone is also referred to herein as the addition of a masked thiol group.

In one embodiment, a cross-linked hyaluronan derivative of the invention containing at least one intramolecular disulfide bond is a water-insoluble gel. A "water-insoluble" gel of the invention, as that and like terms are used herein, is one which is heterogeneous when suspended in a sufficient amount of water at room temperature. Moreover, a cross-linked hyaluronan derivative according to an embodiment containing at least one intramolecular disulfide bond is a hydrogel. As the term is used herein, a "hydrogel" is a cross-linked macromolecular network that swells in water or biological fluids, and exhibits the ability to retain a significant portion of water within its structure without dissolving. As used herein, the term "swelling" refers to the taking up of a liquid, for example water, by a-gel with an increase in volume. Hydrogels have a large molecular weight that generally cannot be measured by conventional methods and are composed of a polymer backbone and cross-links. In one embodiment, the water retained within a hydrogel in its swollen state is entrapped within cellular pockets or compartments formed by polymer network groups. The polymer network groups may be formed as a result of both intramolecular hydrogen bonding and intermolecular hydrogen bonding.

Figure 5:
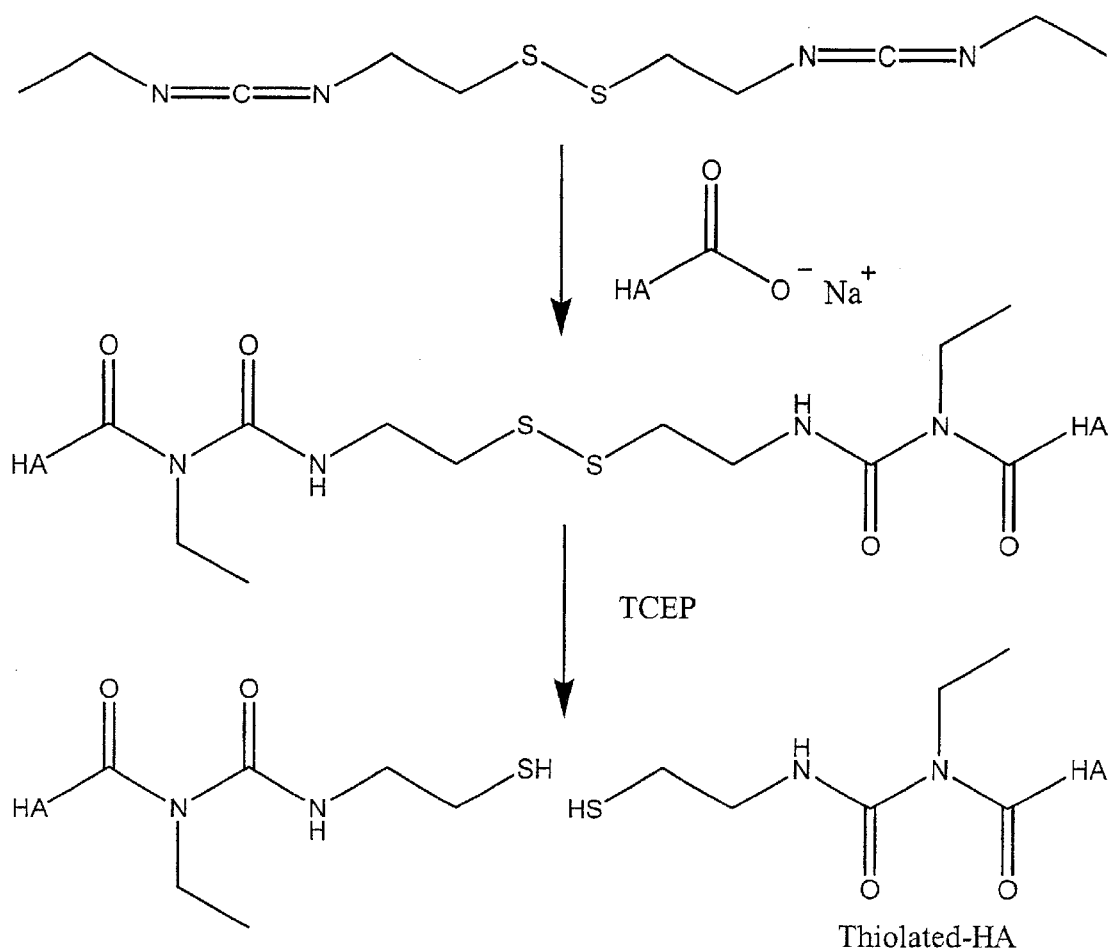
FIG. 5 is a representation of an embodiment of the method of the invention, the cross-linking hyaluronic acid with 2,2'-dithiobis(N-ethyl (N' ethylcarbodiimide)), followed by deprotection of the cross-linked hyaluronic acid derivative with tris(2-carboxyethyl)phosphine hydrochloride (TCEP) to form thiolated hyaluronic acid.

FIG. 5 is a representation of an embodiment of the method of reacting hyaluronic acid with 2,2'-dithiobis(N-ethyl (N'ethylcarbodiimide)) to form a cross-linked hyaluronic acid derivative which is a hydrogel, followed by deprotection of the cross-linked HA derivative with tris(2-carboxyethyl)phosphine hydrochloride (TCEP) to form a thiolated hyaluronan derivative such as, for example, thiolated hyaluronic acid.

Deprotection of Cross-linked Hyaluronic Acid Having an Intramolecular Disulfide Bond According to a Method of the Invention According to an embodiment, a cross-linked hyaluronic acid derivative having an intramolecular disulfide bond is deprotected by reaction with a suitable reducing agent. Reducing the disulfide bridge liberates the masked thiols, producing two-pendant thiol groups per disulfide cross-link along the hyaluronan backbone. The reduction reaction breaks down the hyaluronan hydrogel, decreasing its viscosity. In one embodiment, the cross-linked hyaluronic acid having an intramolecular disulfide bond is deprotected by undergoing a reduction reaction with the reducing agent, tris(2-carboxyethyl)phosphine hydrochloride(TCEP). The reducing agent TCEP has the structural formula:

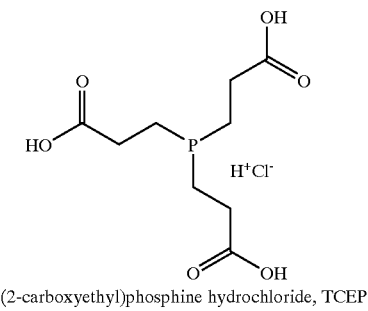

Tris(2-carboxyethyl)phosphine hydrochloride, TCEP

Figure 6:
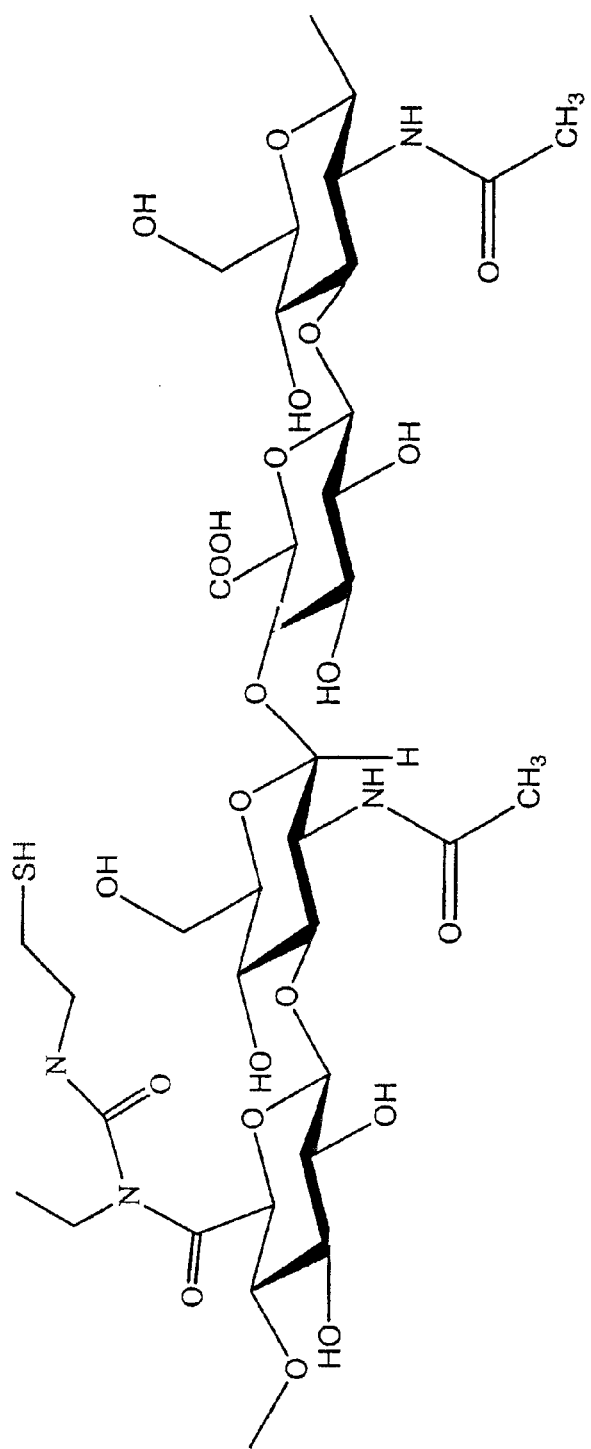
FIG. 6 is a detailed representation of a composition according to an embodiment of the invention, thiolated hyaluronic acid.

A detailed description of one embodiment of a reduction of disulfide bridge cross-linked HA by TCEP to form a hyaluronan derivative having pendant thiol groups is provided below in Example 4. Reduction of the cross-linked hyaluronic acid derivative, according to one embodiment of the invention, produces thiolated hyaluronic acid, a compound of the invention represented by Structural Formula (9). FIG. 6 is a more detailed representation of a portion of the thiolated hyaluronic acid represented by Structural Formula (9).

In another embodiment, the cross-linked hyaluronic acid derivative having an intramolecular disulfide bond is deprotected by undergoing a reduction reaction with the reducing agent, dithiothreitol or the reducing agent 2-mercaptoethanol. In an alternate embodiment, the reducing agent is zinc metal in dilute acid.

In another embodiment, the reducing agent is triphenylphosphine, $(C_6H_5)_3P$, under basic conditions. Triphenylphosphine, a crystalline compound at room temperature, is soluble in ether, benzene, and chloroform, and has been used in the field of polymer chemistry as an initiator of polymerization and organic synthesis. In yet other embodiments, the reducing agent is lithium aluminum hydride, $LiAlH_4$, or sodium borohydride.

According to different embodiments, the pendant thiol groups on the thiolated hyaluronic acid derivative allow a diverse range of modifications to be carried out. Examples of some potential modifications according to several different embodiments are as follows:

Oxidation and Reduction to Reverse the Hydrogel Formation

Figure 7:
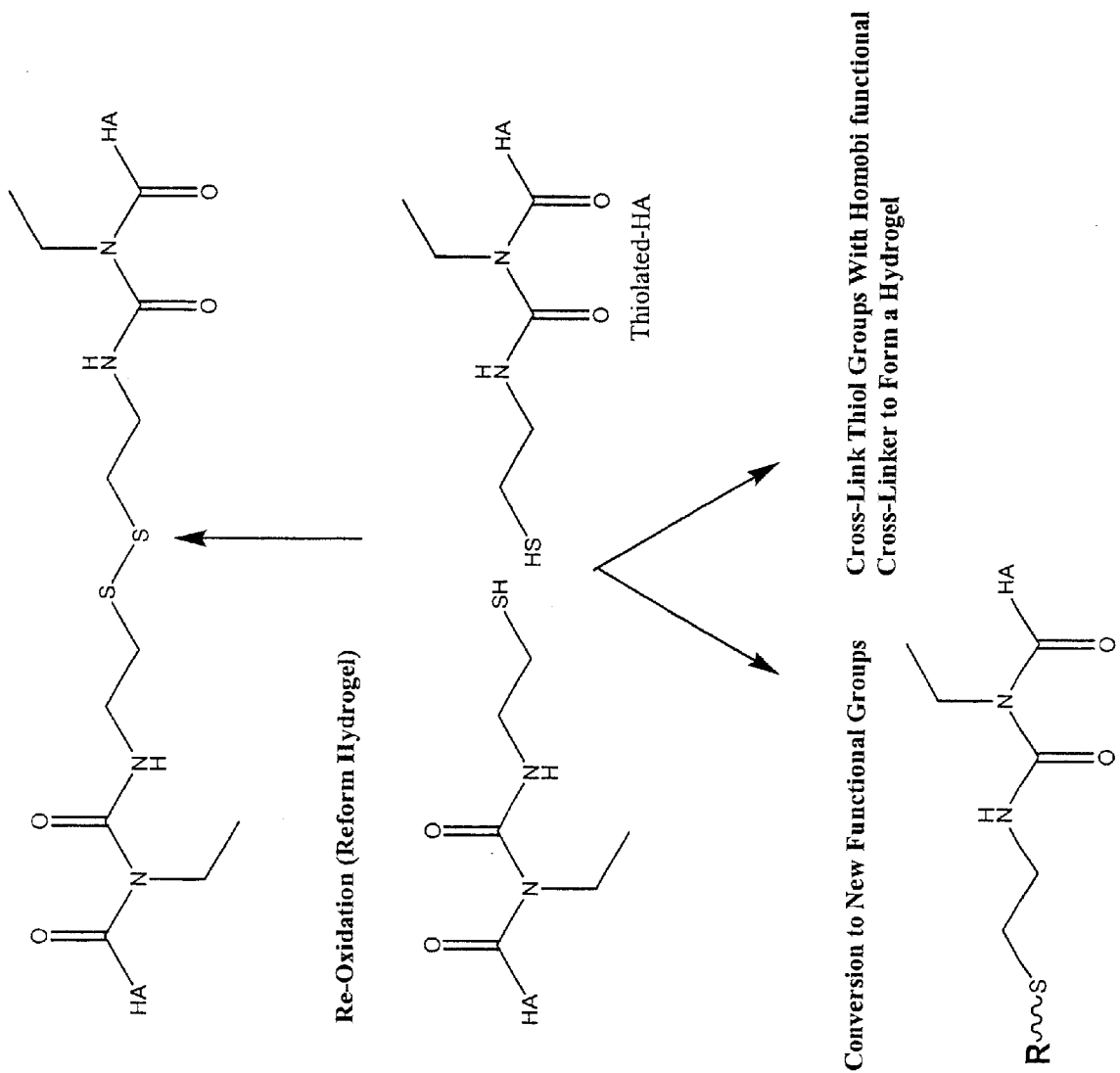
FIG. 7 is a schematic representation of three alternative reactions according to embodiments of the invention: re-oxidation of thiolated hyaluronic acid to re-form a hydrogel; a cross-linking of pendant thiol groups with a homobifunctional cross-linker to form a hydrogel; and a conversion of the sulfhydryl group on thiolated hyaluronic acid to a new functional group, R.
Figure 8:
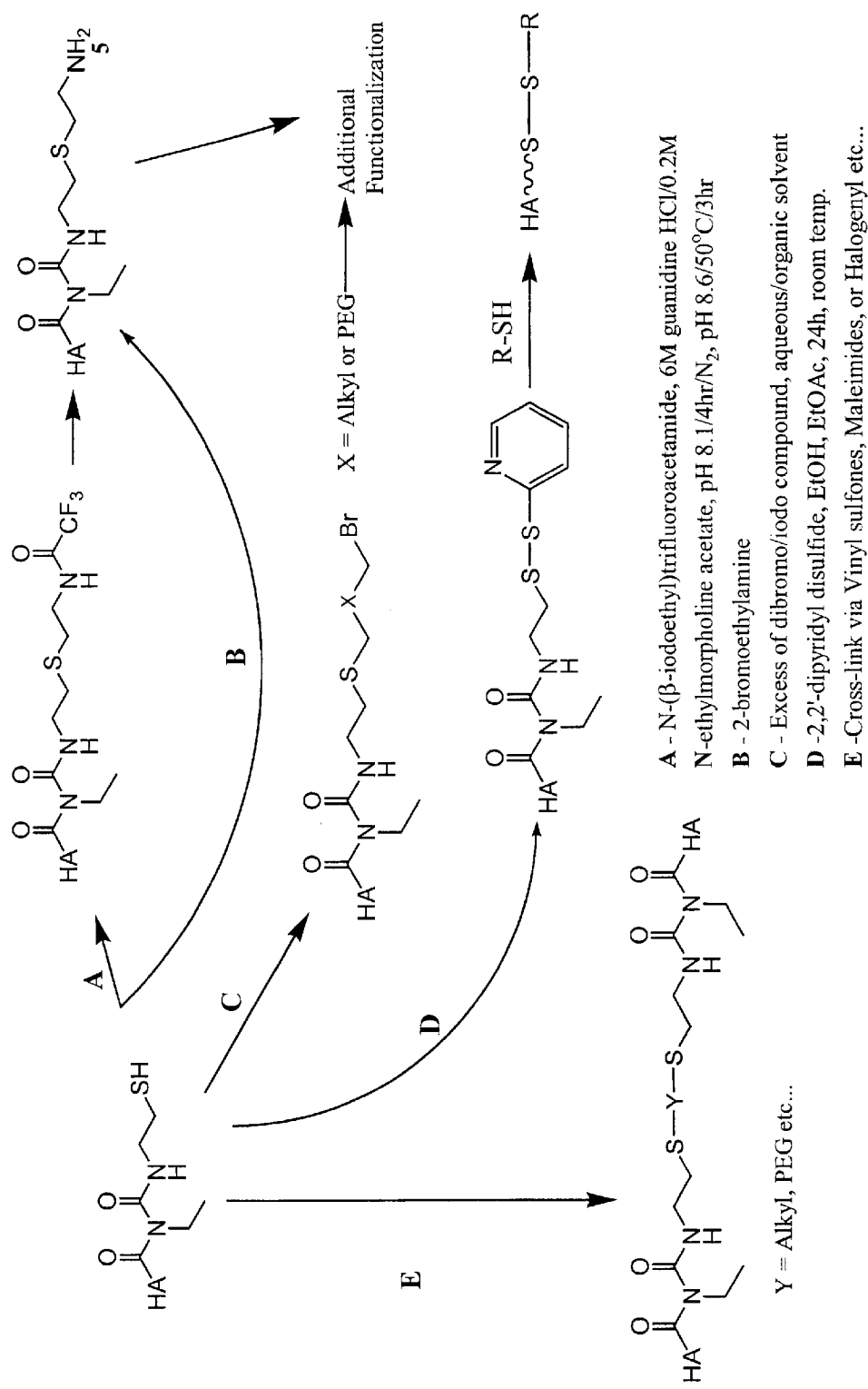
FIG. 8 is a schematic representation of miscellaneous modifications of thiolated hyaluronic acid: (A–E) according to embodiments of the invention.

According to an embodiment, the pendant thiol groups on the thiolated hyaluronic acid may be re-oxidized to form new disulfide bridges, and thus to re-form the original cross-linked hyaluronan hydrogel. See, for example, FIG. 7, which schematically represents the re-oxidation of thiolated hyaluronic acid molecules, each having a pendant thiol group, to form the hyaluronic acid derivative having an intramolecular disulfide bond. An example of an oxidizing agent suitable for use to re-oxidize the pendant thiol groups is a hypochlorite, such as sodium hypoclorite. Other suitable oxidizing agents include, for example, N-bromosuccinimide, 1-chlorobenzothiazole, and N-chloroamidines. This process of reduction and oxidation can be repeated theoretically any number of times. Thus, the formation of the hydrogel is a reversible process.

Cross-linking the Pendant Thiol Groups on Thiolated Hyaluronic Acid With Homobifunctional Sulfhydryl-Reactive Cross-linkers to Form a Hydrogel A hydrogel according to an embodiment of the invention can also be formed by cross-linking pendant thiol groups on the thiolated hyaluronic acid with a homobifunctional cross-linker. A "homobifunctional cross-linker," as the term is used herein, is a cross-linking agent that has two reactive groups that are identical and that are generally located at the ends of an organic spacer group. As is well known to those of skill in the related art, the length of the spacer group is generally chosen to correspond to the distance between the two groups to be linked.

There are two general types of homobifunctional sulfhydryl-reactive cross-linking agents. One type produces an essentially permanent bond with available thiol groups. The second type forms reversible links with available thiol groups. In one embodiment, cross-linking the pendant thiol groups on the thiolated hyaluronic acid with homobifunctional cross-linkers can also form hydrogels in situ by rapid, controllable, and reversible cross-linking of the hyaluronan derivative.

Homobifunctional sulfhydryl-reactive cross-linking agents are frequently referred to in the literature, and are generally commercially available (Pierce Chemical, Rockford, Ill.). An example of homobifunctional sulfhydryl-reactive cross-linking agents suitable for use in an embodiment of the compositions and methods of the invention includes 5-thio-2-nitrobenzoic acid (TNB), which forms a reversible disulfide linkage with a sulfhydryl-containing macromolecule.

Other embodiments employ bis-mercurial salts, bis-thiosulfonates, bis-alkylhalides, and bis-maleimide derivatives. Other embodiments employ dithiobis (succinimidylproprionate) and 3,3'-dithiobis (sulfosuccinimidylproprionate).

In yet another embodiment, the water-insoluble, homobifunctional cross-linker, 1,4-di-(3'-(2'-pyridyldithio)propionamido)butane(DPDPB) is used. Those of skill in the art know that a water-insoluble cross-linker such as DPDPB is dissolved first in an organic solvent, prior to addition of the cross-linker to an aqueous, buffered reaction medium. In another embodiment, bismaleimidohexane (BMH) is used as a cross-linker.

The viscosity of the hyaluronic acid derivative of the invention can be varied in situ by manipulation of the size and nature of the cross-link. Thus, in a particular embodiment, the properties and reactivities of a hydrogel of the invention towards a given biological system can be affected. For example, thiolated hyaluronan of the invention can form both intramolecular and intermolecular disulfide bridges, by cross-linking the material in the presence of certain bioactive agents or cells under mild conditions. These cross-linked compositions can be subsequently uncross-linked under equally mild conditions. As a result, the hyaluronic acid derivatives according to an embodiment have variable viscosities, and the compositions containing the derivatives can reversibly viscosify in response to mild changes in conditions in vivo. By "reversibly viscosify" is meant that the viscosity can be increased or decreased, changing a composition, according to an embodiment of the invention, from a liquid state to a gel state, and from the gel state back to the liquid state. Thus, by varying conditions in vivo, formulations of a composition, according to an embodiment of the invention, can be manipulated to vary the Theological properties of the composition.

The in situ-variable viscosity of the hyaluronic acid derivatives of the invention can be employed in ophthalmic uses such as, for example, filling an intraocular cavity during eye surgery. A composition, according to an embodiment of the invention, can be delivered to the eye in a highly viscous form, similar to that in prior uses of hyaluronic acid compositions. The hyaluronic acid derivative of the invention, like currently available compositions, has sufficiently high viscosity, stability and resilience to perform its intended function. Subsequently, its viscosity can be reduced by disrupting intermolecular disulfide groups between pendant thiol groups. As the attractions between disulfide groups are disrupted, the resulting low viscosity, low molecular weight material produced is cleared from the eye with a significantly reduced likelihood of causing intraocular spikes (IOPs).

The in situ-variable viscosity of the hyaluronic acid derivatives of the invention also provides an advantage when the derivatives are used for tissue engineering. For example, according to one embodiment, a hydrogel composition comprising a cross-linked hyaluronic acid derivative containing an intramolecular disulfide bond is used as a scaffold or matrix for tissue engineering in vitro. According to another embodiment, a hydrogel composition comprising a cross-linked hyaluronic acid derivative containing an intramolecular disulfide bond is used as a scaffold or matrix for tissue engineering in vivo. After cells have been allowed to grow on the hydrogel composition, the HA derivative hydrogel can be reduced under mild conditions, releasing the cells. In addition, in one embodiment, the invention is used for delivery of in situ cross-linkable materials. For example, hyaluronic acid derivatives of the invention containing pendant thiol groups can be mildly cross-linked, forming a hydrogel, in the presence of cells. These cells can be recovered in an equally mild manner by reduction of the hydrogel.

Conversion of Pendant Thiols on the Hyaluronic Acid Derivative of the Invention to New Functional Groups According to one embodiment, pendant thiol groups on a hyaluronic acid derivative can be converted to new functional groups. For example, small molecules such as drugs, rheology modifiers, peptides, radionuclides, and biological probes can be modified in either of two ways and attached to the hyaluronan backbone through reaction with the pendant thiol groups.

In one embodiment, the small molecule is modified to carry a thiol group. The thiol group on the small molecule then attaches to the thiol group of the hyaluronan derivative by forming a disulfide bridge thereto.

In another embodiment, the small molecules are modified to each carry a thiol-reactive group such as, for example, an alkyl halide (iodide or bromide), vinyl sulfone, maleimide, a metal nuclide or a radionuclide. Through methods well known to those of skill in the related art, the thiol-reactive group on the small molecule is reacted with the pendant thiol group on the hyaluronic acid derivative of the invention, thereby converting the thiol group to a new functional group. Examples of thiolation methods are described in "Application of cystamine and N,N-bis (glycyl) cystamine as linkers in polysaccharide-protein conjugation," Odo de Weers et al., *Bioconjugate Chemistry*, 9: 309–315 (1998); "Development of controlled drug release systems based on thiolated polymers," Bernkop-Schnürch, A. et al., *Journal of Controlled Release*, 66: 39–48 (2000); and Wu et al., *Bioconj. Chem.* 10 (6): 921–924 (1999), the teachings of which are incorporated herein by reference in their entireties.

In a particular embodiment, a pendant thiol on a hyaluronic acid derivative is converted to a pendant amine by reaction of the thiol with N-($\beta$-iodoethyl)trifluoroacetamide (m.w. 267) (aminoethyl-8™ reagent, Pierce Chemical, Rockford, Ill.). A protocol is described in Hennanson, Greg T, "Creating Specific Functional Groups," *Bioconjugate Techniques*, Academic Press, Inc., Harcourt Brace & Co. (San Diego, Calif.), pp. 104–105 (1996), the teachings of which are incorporated herein by reference. A protocol is also described in Schwartz W. E., et. al., "N-($\beta$-iodoethyl) trifluoroacetamide: A new reagent for the aminoethylation of thiol groups in proteins," *Anal. Biochem*, 106:43–48 (1980), the teachings of which are incorporated herein by reference. This cationic site may serve as a noncovalent, ionic binding site for anionic substances such as non-steroidal anti-inflammatory drugs (e.g. naprosyn).

In another embodiment, a pendant thiol on a hyaluronic acid derivative is converted to a pendant amine by reaction of the thiol with 2-bromoethylamine (m.w. 123.92), according to a protocol outlined in Hermanson, Id., at 106–107, the teachings of which are incorporated herein by reference. A protocol is also described in Lindley, H., "A new synthetic substrate for trypsin and its application to the determination of the amino acid sequence of proteins," *Nature*, 178:647 (London, 1956), the teachings of which are incorporated herein by reference.

According to another embodiment, a pendant thiol on a hyaluronic acid derivative is converted to a pendant carboxylate by reaction of the thiol with iodoacetic acid. The reaction of a thiol with iodoacetic acid is well known to those of skill in the relevant art.

According to yet another embodiment, a pendant thiol on a hyaluronic acid derivative is converted to a boronic acid by reaction with 3-maleimidophenyl boronic acid (MPBA). In one embodiment, the pendant boronic acid forms a reversible gel complex with cis diols found in glycoproteins and ribonucleotides. The boronic acid-cis diol complex can be dissociated by lowering the pH to 4.5, thereby reversing the gel formation. According to one embodiment, the complex is used to deliver therapeutic agents that are glycoprotein-based or RNA/DNA based.

The residence time of unmodified or native HA in the human body is generally less than a week. However a hyaluronic acid derivative according to an embodiment having at least one intramolecular disulfide bond has a residence time greater than that of native HA. In addition, a thiolated hyaluronan composition according to an embodiment, having an intermolecular disulfide bond between pendant thiol groups also has a longer residence time than native, uncross-linked HA. In general, an increase in the degree of either intermolecular or intramolecular cross-linking results in an increase in the time of residence. By controlling the degree of cross-linking, according to another embodiment, a cross-linked HA of desired residence time can by synthesized. By reducing fewer than all of the disulfide bonds of a cross-linked hyaluronan, a thiolated hyaluronan according to an embodiment is produced that has increased residence time because it has both intramolecular and intermolecular disulfide bridges. By attaching a small molecule such as a bioactive molecule or drug to at lease one of the pendant thiol groups on the hyaluronan having at least one intramolecular disulfide bridge, as described above, a sustained or controlled-release drug-delivery vehicle according to an embodiment, with controlled residence time is formulated.

The hyaluronan derivative according to an embodiment of the invention described above can function as a vehicle which provides the controlled or sustained release of a drug. According to one embodiment, the controlled-release drug-delivery vehicle is then placed in contact with a pre-selected tissue, and allowed to remain in place until a desired clinical result is achieved. The controlled-release drug-delivery vehicle according to an embodiment may be injected or implanted at the locus where delivery is desired, or may be administered orally or by a route that is a combination of two or more of these administration routes.

The linkage between the therapeutic drug moiety and the hyaluronan derivative can be readily broken, releasing the therapeutic drug at the site of administration. The more stable chemical bond between the HA molecule and the carbodiimide moiety will ensure the release of the therapeutic drug without the release of the carbodiimide residue. The release of the carbodiimide residue might affect the therapeutic action of the drug.

Diffusion provides the delivery of a drug via delivery systems in which the drug non-covalently interacts with the derivatized HA or other pharmaceutical carrier. Such non-covalent interactions include ionic, hydrophobic, and hydrophilic interactions in which the drug is dispersed within the carrier. As used herein, the term "dispersed" shall refer to ionic, hydrophobic, and hydrophilic interactions between the drug and the hyaluronan derivative or other carrier.

The rate of delivery of a drug or other bioactive agent is related not only to the rate of its diffusion, but also to the rate of degradation of the hyaluronan derivative to which the drug or other bioactive agent is attached covalently, or in which the drug or other bioactive agent is dispersed. The rate of degradation of the hyaluronan derivative is related to the degree of cross-linking and is also dependent on numerous metabolic processes taking place in vivo The degradation process is usually slower than diffusion. By choosing the concentration of the drug bonded to the derivatized HA or dispersed within the derivatized HA, and the degree of cross-linking, one can control the rate of degradation and diffusion and, thus, the rate of drug delivery.

The drug concentration can be varied over very broad limits and preferably should be chosen depending on the degree of cross-linking of the derivatized HA, the solubility of the drug, its pharmaceutical activity, and the effect desired.

Any substance which has biological or pharmaceutical activity and which is normally considered to be a drug can be used as the drug component in a pharmaceutically active moiety of a hyaluronic acid derivative of the invention. Pharmaceutically-active substances suitable for use in an embodiment include, but are not limited to, analytes, growth factors, enzymes, therapeutic drugs, biopolymers, anti-microbials, and deodorant agents.

In an embodiment that is a compound represented by Structural Formula (10) and salts thereof:

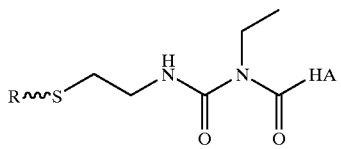

wherein R is a drug or pharmaceutically active moiety, the pharmaceutically active moiety may be, for example, an analyte, a growth factor, an enzyme, a therapeutic drug, a biopolyner, an anti-microbial, or a deodorant agent.

A "therapeutic drug," as that term is used herein, includes, for example: compounds and compositions recognized in the official United States Pharmacopoeia, the official Homeopathic Pharmacopoeia of the United States, or the official National Formulary, or any supplement of any of them; compounds and compositions intended for use in the diagnosis, cure, mitigation, treatment, or prevention of disease in man or other animals; and compounds and compositions (other than food) intended to affect the structure or any function of the body of man or other animals.

Examples of classes of therapeutic drugs include steroidal and non-steroidal anti-inflammatory drugs, hormones and any synthetic analogues and pharmaceutically-active fragments thereof Thus, in one embodiment, R in a compound represented by Formula (10) is an anti-inflammatory drug, a hormone, or any synthetic analogue or pharmaceutically-active fragment of the anti-inflammatory drug or hormone.

Therapeutic drugs which are suitable for use in delivery systems in embodiments of the invention may be fat soluble, water-soluble, anionic or cationic, as long as they can interact with a group on the hyaluronic aid derivative of an embodiment to form either covalent or ionic bonds or hydrophobic or hydrophilic interactions, including those described below.

According to an embodiment, a hydrophobic interaction between a therapeutic drug having a hydrophobic moiety and the hyaluronan derivative according to an embodiment can occur. Examples of drugs having hydrophobicity and suitable for use in an embodiment include fatty acid derivatives, steroids (e.g., dexamethasone) and their analogs.

The delivery system of the invention is well-suited for administering growth factors (e.g., interleukins, prostaglandins, thromboxanes, leukotrienes and cytokines), steroidal and non-steroidal contraceptive agents, antibiotics (e.g., penicillin, streptomycin and linocomycin), analgesics, sedatives, barbiturates, aminoalkybenzenes, catecholamines, narcotics, narcotic antagonists, anti-neoplastic agents and anticoagulants (e.g., heparin and heparin sulfate). Thus, in one embodiment, R in a compound represented by Formula (10) is a growth factor such as, for example, an interleukin, a prostaglandin, thromboxane, leukotriene or a cytokine. In another embodiment, R in a compound represented by Formula (10) is a contraceptive agent, an antibiotic, an analgesic, a sedative, a barbiturate, an aminoalkybenzene, a catecholamine, a narcotic, a narcotic antagonist, an anti-neoplastic agent, or an anticoagulant.

The following are examples of the invention, and are not intended to limit the scope of the invention in any way.

EXEMPLIFICATION

Example 1

Synthesis of the Masked Thiol-containing Biscarbodiimide of the Invention

To a solution of cystamine (2.826 g, 18.56mmol) in chloroform (15mL) was added dropwise ethyl isothiocyanate (2.05 mequiv, 3.235 g, 37.12 mmol) in chloroform (15mL). The solution was stirred for 4 hours, at which time a white precipitate formed. The precipitate was collected by filtration and washed with cold chloroform (3×5mL). The precipitate, 2,2'-dithiobis (N-ethyl (N'-ethylthiourea)), was dried under vacuum and used without further purification. To a solution of 2,2'-dithiobis(N-ethyl (N'-ethylthiourea)) (200 mg, 6.12 mmol) suspended in chloroform (8 mL) was added IN sodium hydroxide (2 mL) and sodium hypochlorite (10–13% available chlorine) (0.75 mL). The two-phase system was shaken for 3 minutes and the chloroform layer isolated. The organic solvent was removed under reduced pressure to yield a yellow oil, 2,2'-dithiobis (N-ethyl (N'-ethylcarbodiimide)).

Example 2

Cross-linking of High Molecular Weight Hyaluronan with 2,2'-dithiobis (N-ethyl(N'-ethylcarbodiimide))

Hyaluronic acid (600 mg, 1.5 mmol) was dissolved in distilled water (120 mL) and the pH adjusted to 4.75 using 0.1N HCl. 2,2'-dithio bis(N-ethyl(N-ethylcarbodiimide)) (116.3 mg, 0.45 mmol, 30 mol%) dissolved in acetone (58 mL, 2 mg/mL) was added. The pH was allowed to rise to 5.8, then gradually reduced back to 4.75 over a period of 3 hours, by dropwise addition of 0.1N HCl. The reaction mixture was made up to 5% NaCl (6 g) and stirred for 30 minutes at a room temperature of about 20° C. The reaction mixture was poured onto ethanol (360 mL, 3 volume equivalents with respect to the aqueous volume). The precipitate was collected by filtration and dried under reduced pressure yielding 610 mg of product, a cross-linked hyaluronic acid derivative having an intramolecular disulfide bond.

Example 3

Synthesis of 2,2'-dithiobis (N-ethyl(N'-ethylcarbodiimide))—(BCDISS) via the Urea Route
a) Synthesis of 2,2'-dithiobis([N-ethyl(N'-ethylurea)) Intermediate In a 50 mL round bottom flask, cystamine (1.0 g, 6.57 mmol) was dissolved in chloroform (30 mL). To the resulting solution was added in one aliquot, ethyl isocyanate (2.5 mequivs, 16.43 mmol, 1.167 g, 1.300 mL). The atmosphere was replaced with nitrogen; the flask was sealed; and the reaction was allowed to proceed for 16 hours. The chloroform was removed under reduced pressure, yielding a viscous oil. Methanol (20 ml) was added, and the oil scratched, yielding a white precipitate. The mixture was heated to dissolve the precipitate, then filtered. On cooling, a white crystalline powder formed, 2,2'-dithiobis (N-ethyl(N'-ethylurea)), which was separated and dried under high vacuum.

b) Synthesis of 2,2'-dithiobis (N-ethyl(N'-ethylcarbodiimide))

2,2'-dithiobis (N-ethyl(N'-ethylthiourea)) (1.0 g, 3.06 mmol) was dissolved in pyridine (25 mL) in a 100 mL round bottom flask. Next, p-toluenesulfonyl chloride (2.2 mequivalents, 6.74 mmol, 1.284 g) was dissolved in pyridine (10 mL) and placed in a pressure-equalizing funnel. The reaction system was placed under nitrogen and the tosyl chloride solution added dropwise. The reaction mixture was stirred for 4 hours, then poured onto water (215 mL). The aqueous solution was extracted with chloroform (3×75 mL). The chloroform was dried (MgSO$_4$) and the solvent was removed under reduced pressure, yielding an oily product, 2,2'-dithiobis (N-ethyl(N'-ethylcarbodiimide)). The product was re-dissolved in acetone (100 mL).

Example 4

Deprotection of a Cross-linked Hyaluronic Acid Derivative Having an Intramolecular Disulfide Bond, the Derivative Made According to Example 2.

The disulfide bridge cross-linked HA was reduced to thiol-modified HA as follows. HA derivative(200 mg), cross-linked with a biscarbodiimide having an intramolecular disulfide bond, was suspended in 0.1 M phosphate buffer (pH 4.5–7.5; preferably pH 6.5–6.8) at 5 mg/mL (40 mL). TCEP- HCl (28.7 mg, 0.1 mmol, large excess) was added to the disulfide-modified HA solution and stirred for 20 minutes at room temperature (about 20–25° C.). NaCl (2 g) was added to the solution to give a 5% NaCl w/v solution and stirring was continued for 5 minutes. The solution was poured onto ethanol (120 mL) to precipitate the reduced thiol-modified HA. The precipitate was collected and washed in 80% ethanol for 15 minutes. The precipitate was removed from the wash solution and dried under reduced pressure for 3 to 4 hours, producing an HA derivative having pendant thiol groups.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A cross-linked hyaluronan derivative containing at least one intramolecular disulfide bond, wherein the cross-linked hyaluronan derivative is a product of a reaction between the precursor of the cross-linked hyaluronan derivative and a biscarbodiimide having an intramolecular disulfide bond.

2. A cross-linked hyaluronan derivative containing at least one intramolecular disulfide bond, wherein the cross-linked hyaluronan derivative is a product of a reaction between hyaluronic acid or a salt thereof and a biscarbodiimide having an intramolecular disulfide bond.

3. A cross-linked hyaluronan derivative containing at least one intramolecular disulfide bond, wherein the cross-linked hyaluronan derivative is a product of a reaction between hyaluronic acid or a salt thereof and a biscarbodiimide having a structure represented by Structural Formula (1):

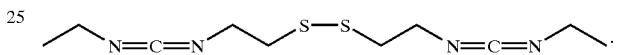

4. The cross-linked hyaluronan derivative of claim 1, wherein the derivative is biocompatible.

5. The cross-linked hyaluronan derivative of claim 1, wherein the derivative is biodegradable.

6. A compound represented by Structural Formula (8) and salts thereof:

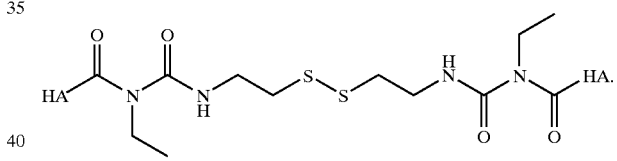

* * * * *